United States Patent [19]

Nugent, Jr.

[11] Patent Number: 5,352,836
[45] Date of Patent: Oct. 4, 1994

[54] ENANTIOSELECTIVE LEWIS ACID CATALYSTS OF THE EARLY TRANSITION METALS

[75] Inventor: William A. Nugent, Jr., Wilmington, Del.

[73] Assignee: E. I. Du Pont de Nemours and Company, Wilmington, Del.

[21] Appl. No.: 47,393

[22] Filed: Apr. 19, 1993

Related U.S. Application Data

[62] Division of Ser. No. 693,896, May 1, 1991, Pat. No. 5,231,203.

[51] Int. Cl.$^5$ ............................................ C07C 215/00
[52] U.S. Cl. ...................................... 564/506; 564/503
[58] Field of Search .................................. 564/503, 506

[56] References Cited

U.S. PATENT DOCUMENTS

| | | | |
|---|---|---|---|
| 2,824,114 | 2/1958 | Bostwick | 260/429.3 |
| 3,926,867 | 12/1975 | Quock et al. | 260/2.5 AM |
| 4,254,291 | 3/1981 | Kane | 568/875 |
| 4,281,201 | 7/1981 | Abend | 564/506 |

OTHER PUBLICATIONS

K. Narasaka, *Synthesis*, pp. 1–11 (Jan. 1991).
J. K. Whitesell, *Chem. Rev.*, 89:1581–1590 (1989).
R. Taube et al., *Anorg. Allg. Chem.* 581:89–98, (1990).
A. I. Astakhov et al., *Izv. Vyssh. Ucheb. Zaved., Khim, Tekhnol*, 15:1620 (1972) (Chem. Abstracts, 78:66407e (1973).
R. C. Mehrota et al., *J. Indian Chem. Soc.,* 44(6):467–472 (1967).
R. C. Mehrota, et al., *Indian J. Chem.*, 5:505–507 (1967).
Chem. Abstr. 91:402891m (1979).
S. N. Tandura et al., *Zh. Obsch. Chem.* 54(9):2012–2017 (1984). (English Trans. p. 1795).
*Chem. Abstr.*, 67:64321(w) (1967).
J. D. Morrison et al., "Asymmetric Reactions and Processes in Chemistry", A. C. S. Symposium Series, No. 185, Washington D.C. (1982).
M. Grassi et al., *Tetrahedron* 41(1):177–181 (1985).
D. Seebach, *Helvetica Chimica Acta.* 70:954–974 (1987).
M. Emziane et al., *Organometal. Chem.* 346:C7–C10 (1988).
Y. Yamashita, *Bull. Chem. Soc. Japan.*, 61:1213–1220 (1988).
S. Matsubara et al., *Tetrahedron Letters.*, 31(43):6209–6212 (1990).
M. T. Reetz et al., *Chem. Ind.*, p. 824 (Dec. 1986).
K. Narasaka et al., *Chem. Lett.* pp. 2073–2076 (1987).
M. Hayashi et al., *J. Chem. Soc., Chem. Commun.* pp. 1364–1365 (1990).
R. Noyori et al., *Chem. Int. Ed. Engl.* 30:49–69 (1991).
P. A. Chaloner et al., *Tetr. Lett.* 31(36):5185–5188 (1990).
M. Yoshioka et al., *Tetr. Lett.* 30(13):1657–1660 (1989).
B. Schmidt et al., *Angew. Chem. Int. Ed. Engl.* 30:99–101 (1991).
M. Y. Reetz et al., *Tetr. Lett.* 27:5711–5714 (1986).

*Primary Examiner*—José G. Dees
*Assistant Examiner*—Porfirio Nazario-Gonzalez
*Attorney, Agent, or Firm*—Kathleen W. Geiger

[57] ABSTRACT

Optically active Lewis acid catalysts of the early transition metals which are useful in the catalysis of asymmetric additions have been prepared. The catalyst complexes comprise an alkoxide of a group IV or group V metal and an optically active trialkanolamine or dialkanolamine ligand.

4 Claims, No Drawings

ENANTIOSELECTIVE LEWIS ACID CATALYSTS OF THE EARLY TRANSITION METALS

This is a division of application Ser. No. 07/693,896, filed May 1, 1991, now U.S. Pat. No. 5,231,203.

FIELD OF THE INVENTION

This invention relates to enantioselective Lewis acid catalyst complexes of the early transition metals and the process of preparation thereof. The complexes comprise an alkoxide of a group IV or group V transition metal and an optically active di- or trialkanolamine.

BACKGROUND OF THE INVENTION

One of the principal goals of modern organic chemistry is the development of new synthetic routes toward the controlled, efficient production of asymmetric compounds. Saturated carbon atoms, which constitute the backbone of most organic compounds, are attached to adjacent atoms through a tetrahedral arrangement of chemical bonds. If the four bonds are to different atoms or groups, the central carbon provides a chiral, or asymmetric center, and the compound therefore may have the ability to exist in two mirror-image, or enantiomeric forms. When synthetic organic chemists attempt preparation of these asymmetric compounds it is crucial to have a means to produce the desired enantiomer because compounds of the wrong enantiomeric form often lack the desired biological, physical or chemical properties. The present invention thus focuses on enantioselective acid catalysts, which are shown to provide a means toward the synthesis of compounds in a desired enantiomeric form.

The literature contains a number of reports of research on chiral Lewis acids and the results are summarized in a recent review paper (Narasaka, K., Synthesis, 1991, 1). Transition metal catalysts designed for this purpose in general contain bidentate diol ligands as the source of chirality. This reflects the "fundamental concept" that such "C$_2$ symmetry" ligands will provide especially high enantioselectivity (Whitesell, J. K., Chem. Rev. 1989, 89, 1581). Accordingly, there have been no reported attempts to use optically active trialkanolamines, which lack C$_2$ symmetry, as chiral ligands in asymmetric Lewis acids.

Previous research on early transition metal trialkanolamine complexes focused on compounds containing achiral triethanolamine. For example, complexes have been described containing derivatives of titanium (Bostwick, C. O., U.S. Pat. No. 2,824,114 (1958); Chem. Abstr. 1958, 52, 7743], zirconium (Taube, R.; Knoth, P. Z., Anorg. Allg. Chem. 1990, 581, 89), vanadium (Astakhov, A. I.; Kas'yanenko, A. I., Izv. Vyssh. Ucheb. Zaved., Khim. Khim. Tekhnol. 1972, 15, 1620 (Chem Abstracts, 1973, Vol.78 No. 66407)), niobium [Mehrota, R. C.; Kapoor, P. N., J. Indian Chem. Soc. 1967, 44, 467), and tantalum (Mehrota, R. C.; Kapoor, P. N., Indian J. Chem. 1967, 5, 505). There is an extensive literature on catalytic uses of triethanolamine titanate, for example, for cross-linking epoxy resins (Bokalo, G. A.; Omel'chenko, S. I.; Zapunnaya, K. V., Vysokomol. Soedin., Set. B. 1979, 21, 371. Chem. Abstr. 1979, 91, 40289), and at least one catalytic application of a triethanolamine vanadate (Kane, B. J., U.S. Pat. No. 4,254,291 (1981). Chem. Abstr. 1981, 94, 47554).

Also known in the art are examples of chiral but racemic trialkanolamine complexes. These include a vanadium complex of triisopropanolamine (Tandura, S. N.; Voronkov, M. G.; Kisin, A. V.; Shestakov, E. E.; Ovchinnikova, Z. A.; Baryshok, V. P., Zh. Obsch. Chem. 1984, 54, 2012 (English Trans. p 1795)) as well as titanium analogues (Voronkov, M. G.; Faitel'son, F. D., Khim. Geterosikl. Soedin. 1967, 39. Chem. Abstr. 1967, 67, 64321).

One reported complex of an early transition metal with an optically active trialkanolamine involves a ligand wherein the asymmetry resides in only one "arm" of the trialkanolamine, and the asymmetric carbon is bound to nitrogen (Liu, H.; Yin, C. Gaodeng Xuexiao Huaxue Xuedbao 1989, 10, 1257. Chem. Abstr. 1989, 113, 125232).

Other related art includes two reports of borate esters of enantiomerically pure triisopropanolamine Morrison, J. D.; Grandbois, E. R.; Weisman, G. R. in "Asymmetric Reactions and Processes in Chemistry" (A.C.S. Symposium Series, No. 185) American Chemical Society, Washington, DC, 1982; Grassi, M.; DiSilvestro, G.; Farina, M. Tetrahedron 1985, 41, 177). The first of these papers describes the use of the corresponding borohydride as a stoichiometric chiral reducing agent.

Early transition metal complexes containing the achiral dialkanolamine diethanolamine are likewise known (Mehrota, R. C.; Kapoor, P. N., J. Indian Chem. Soc. 1967, 44, 467; Indian J. Chem. 1967, 5, 505).

The asymmetric addition of azidotrimethylsilane is the subject of two reports. In the first, titanium isopropoxide was treated with various chiral diols or aminoalcohols in an effort to obtain a homogeneous catalyst (Emziane, M.; Sutowardoyo, K. I.; Sinou, D., J. Organometal. Chem. 1988, 346, C7). The catalytic addition proceeded but the product was essentially racemic. A modest enantiomeric excess ("ee") was obtained by running the reaction stoichiometrically. The other report uses transition metal tartrates as heterogeneous catalysts (Yamashita, Y., Bull. Chem. Soc. Japan 1988, 61, 1213). Using zinc tartrate, a 42% ee was claimed for a 14 day reaction.

There are also many reports of catalytic addition of trimethylsilyl cyanide to epoxides (Matsubara, S.; Onishi, H.; Utimoto, K., Tetrahedron Lett. 1990, 31, 6209) but no reports of asymmetric additions. On the other hand, the asymmetric addition of trimethylsilyl cyanide to aldehydes has been reported by three research groups (Reetz, M. T.; Kyung, S. -H.; Bolm, C.; Zierke, T., Chem. Ind. (London), 1986, 824; Narasaka, K.; Yamada, T.; Minamikawa, H., Chem. Lett. 1987, 2073; Hayashi, M.; Matsuda, T.; Oguni, N., J. Chem. Soc., Chem. Commun. 1990, 1364). All three examples involve the use of titanium alkoxides as homogeneous asymmetric catalysts.

A significant body of research on the asymmetric catalysis of the addition of organometallic reagents such as diethylzinc to carbonyl compounds exists and this research has been summarized in a recent review (Noyori, R.; Kitamura, M., Angew. Chem., Int. Ed. Engl. 1991, 30, 49). These procedures typically involve adding an optically active aminoalcohol to a mixture of diethylzinc and the carbonyl compound with no early transition metal being present. In one case an optically active dialkanolamine has been used for this purpose, again in the absence of an early transition metal (Chaloner, P. A.; Langadianou, E., Tetr. Lett. 1990, 36, 5185). On the other hand, optically active titanium complexes have been used to catalyze the asymmetric addition of diethylzinc to aldehydes (Yoshioka, M.;

Kawakita, T.; Ohno, M., Tetr. Lett. 1989, 30, 1657; Schmidt, B.; Seebach, D., Angew. Chem., Int. Ed. Engl. 1991, 30, 99). In these cases the ligands are diols or diamides of $C_2$ symmetry. In one case, a methyl-titanium complex coordinated to an N-sulfonated derivative of an aminoalcohol has been used for the stoichiometric alkylation of aldehydes (Reetz, M. T.; Kuekenhoener, T.; Weinig, P ., Tetr. Lett. 1986, 27, 5711).

Thus, although significant advances have been made in the field of asymmetric catalysis, a clear need exists for the development of new procedures for the controlled organic synthesis of asymmetric compounds. It is the object of this invention to provide a new class of chiral Lewis acid catalysts which will be useful in the preparation of asymmetric products.

SUMMARY OF THE INVENTION

This invention provides optically active group IV or group V transition metal Lewis acid catalyst complexes comprising the formula (1):

$$(M-L)_x(O)_y(OR^4)_z \quad (1)$$

wherein M is a group IV or V transition metal; x is 1 or 2; y is 0 to 3; z is 0 to 3, provided that y and z cannot both be zero in the same compound; $R^4$ is H, or $C_1$ to $C_{20}$ hydrocarbyl; and L is a conjugate base of an optically active trialkanolamine or dialkanolamine comprising formula (2) or formula (3):

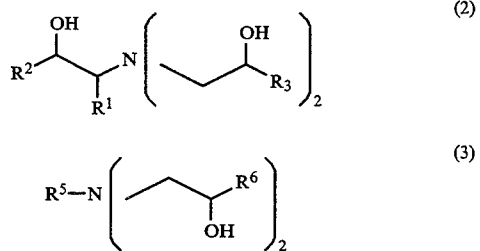

wherein $R^1$ is H or $CH_3$; $R^2$, $R^3$ and $R^6$ are each independently $C_1$ to $C_{20}$ hydrocarbyl which may additionally have halogen, ether, or ester substituent groups; and $R^5$ is H, or $C_1$ to $C_{20}$ hydrocarbyl which may additionally have halogen, ether or ester substituent groups.

This invention also provides an optically active trialkanolamine comprising formula (2):

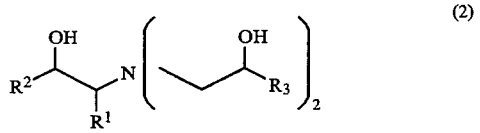

wherein $R^1$ is H or $CH_3$; $R^2$ and $R^3$ are each independently $C_1$ to $C_{20}$ hydrocarbyl which may additionally have halogen, ether, or ester substituent groups; provided that $R^1$ is $CH_3$ when $R^2$ and $R^3$ are each $CH_3$.

This invention also provides a process for the preparation of group IV and V transition metal Lewis acid catalysts comprising: reacting an alkoxide of a group IV or group V transition metal of the formula $M(OR)_n$; wherein M is a group IV or group V transition metal; R is $C_1$ to $C_{20}$ hydrocarbyl; and n is the valence of M in its highest oxidation state (i.e., n is 4 for Ti, Zr, and Hf; and n is 5 for V, Nb, and Ta); with an optically active tri- or dialkanolamine of formula (2) or formula (3):

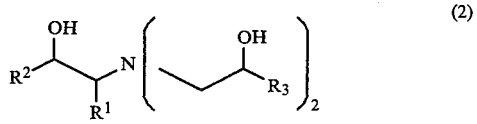

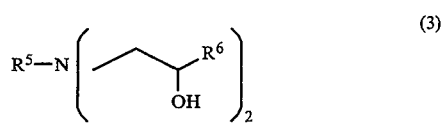

wherein $R^1$ is H or $CH_3$; $R^2$, $R^3$ and $R^6$ are each independently $C_1$ to $C_{20}$ hydrocarbyl which may additionally contain halogen, ether, or ester substituent groups; and $R^5$ is H or $C_1$ to $C_{20}$ hydrocarbyl which may additionally have halogen, ether or ester substituent groups, to yield the desired group IV or V transition metal chiral lewis acid catalyst.

This process further comprises the addition of about 0.1 to 10 molar equivalents of water.

DETAILED DESCRIPTION OF THE INVENTION

Applicant has discovered a method of preparing chiral Lewis acid catalysts of the early transition metals. The procedure involves the reaction of an alkoxide of an early transition metal (Ti, Zr, Hf, V, Nb, or Ta) with an optically active di- or tri-alkanolamine which is chiral at the hydroxyl-bearing carbon atoms. The resultant complex is then optionally treated with from 0.1 to 10 molar equivalents (optimally 1.0 equivalents) of water to give a catalyst which often exhibits enhanced activity and selectivity. The useful trialkanolamines have the structure (2)

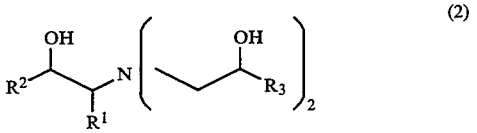

wherein $R^1$ may be hydrogen or a methyl group; and $R^2$ and $R^3$ may be a $C_1$ to $C_{20}$ hydrocarbyl group such as an alkyl, aryl, aralkyl, or alkylaryl group which may additionally have substituents such as halogen, ether, or ester functional groups. Preferred form of the trialkanolamine exists according to formula (2) wherein $R^1$ is H; $R^2$ is $CH_3$; and $R^3$ is $CH_3$.

The useful optically active dialkanolamines have the structure shown by formula (3)

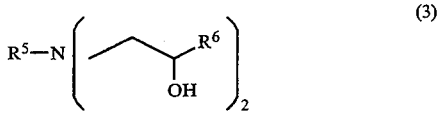

wherein $R^5$ may be H, or may be a $C_1$ to $C_{20}$ hydrocarbyl such as alkyl, aryl, aralkyl or arylalkyl which may additionally have substituents such as halogen, ether or ester groups. $R^6$ may be a $C_1$ to $C_{20}$ hydrocarbyl such as alkyl, aryl, aralkyl or alkylaryl which may additionally have halogen, ether or ester groups.

Preferably, the enantiomeric excess of the trialkanolamine or dialkanolamine ligand is at least about 90%.

Catalyst preparation is preferably carried out in an aprotic organic solvent. Both the starting metal alkoxide and the alkanolamine ligands should be soluble in the solvent. A solvent with a low-boiling point (less than about 150° C.) is preferred to facilitate catalyst isolation. Examples of suitable solvents include, but are not limited to tetrahydrofuran, diethyl ether, benzene, toluene, dichloromethane, 1,2-dichloroethane and the mixtures thereof.

The reactant ratio of tri- or dialkanolamine of formula (2) or (3) to the metal alkoxide is preferably about 1 to 1.

Temperature and pressure conditions for the reaction are not critical. The reaction is preferably carried out from about room temperature up to the boiling point of the solvent. It is most convenient to carry out the reaction at ambient temperature and pressure.

The catalytic complexes produced are typically white solids which can be shown by elemental analysis to have incorporated the di- or trialkanolamine ligand. For the metals Ti, V, Nb and Ta it appears that discrete, characterizable product complexes are produced: However, for the metals Zr and Hf, the structural nature of the catalyst appears to be complex and cannot be shown to correspond to any obvious composition.

Applicant has characterized the general structure of the complexes of the invention according to the formula (1): $(M-L)_x(O)_y(OR^4)_z$; wherein M may be any of the group 4 or group 5 transition metals; L is a conjugate base of a trialkanolamine or dialkanolamine ligand shown by formula (2) or (3); $R^4$ is H or a $C_1$ to $C_{20}$ hydrocarbyl; x is 1 or 2; y is 0 to 3; and z is 0 to 3.

By the term "conjugate base" Applicant means an anionic alkoxide ligand obtained by deprotonating the corresponding di- or trialkanolamine.

By the term "hydrocarbyl" Applicant includes all alkyl, aryl, aralkyl or alkylaryl carbon substituents, either straight-chain, branched or cyclic.

For complexes containing a trialkanolamine ligand when M of the catalyst complex is titanium, the catalyst complex may exist according to the formula (L-Ti) $(OR^4)$. When designated according to the general formula (1), $(M-L)_x(O)_y(OR^4)_z$: M is Ti; L is a conjugate base of a trialkanolamine of formula (2); x is 1; y is 0; and z is 1. Alternatively, when M is titanium the complex may also exist according to the formula (L-Ti)-O-(Ti-L); and when designated by the general formula (1), x is 2; y is 1; and z is 0.

For complexes containing a dialkanolamine when M is titanium the complex may exist according to the formula (L-Ti) $(OR^4)_2$; wherein according to the general formula (1), $(M-L)_x(O)_y(OR^4)_z$: M is Ti; L is a conjugate base of a dialkanolamine of formula (3); x is 1; y is 0; and z is 2. Alternatively, the complex may also exist according to the formula (L-Ti)O_2(Ti-L); wherein according to the general formula (1), M is Ti; L is a conjugate base of a dialkanolamine of formula (3); x is 2; y is 2; and z is 0.

For complexes containing a trialkanolamine when M is vanadium, the complex exists according to the formula (L-V)=(O); and when designated according to the general formula (1), $(M-L)_x(O)_y(OR^4)_z$: M is V; L is a conjugate base of a trialkanolamine of formula (2); x is 1; y is 1; and z is 0.

For complexes containing a trialkanolamine when M is niobium, the complex may exist according to the formula (L-Nb)-(OR)_2; and when designated according to the general formula (1), $(M-L)_x(O)_y(OR^4)_z$: M is Nb; L is a conjugate base of a trialkanolamine of formula (2); x is 1, y is 0, and z is 2. Alternatively the complex may exist according to the formula (L-Nb)O_2(Nb-L)

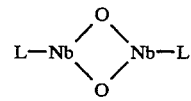

and according to the general formula (1), x is 2, y is 2, and z is 0.

For complexes containing a trialkanolamine when M is tantalum, the complex may exist according to the formula (L-Ta)-(OR)_2; and when designated according to the general formula (1), $(M-L)_x(O)_y(OR^4)_z$: M is Ta, L is a conjugate base of a trialkanolamine of formula (2), x is 1, y is 0, and z is 2. Alternatively the complex may exist according to the formula (L-Ta)O_2(Ta-L)

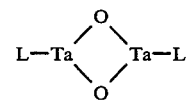

and according to the general formula (1), x is 2, y is 2, and z is 0.

When M is zirconium or hafnium, the complex is described according to the general formula $(Zr-L)_x(O)_y(OR^4)_z$ or $(Hf-L)_x(O)_y(OR^4)_z$; wherein L is a conjugate base of a trialkanolamine of formula (2) or a dialkanolamine of formula (3); x is 1 or 2; y is 0 to 3; and z is 0 to 3; provided that y and z cannot both be zero in the same catalyst complex (i.e., y+z is greater than zero).

The chiral Lewis acid catalyst complexes of the invention are useful in the catalysis of reactions producing asymmetric products. The optically active trialkanolamines of the invention are useful, for example, in the formation of the catalytic complexes of the invention. The process of the present invention is useful for the preparation of chiral Lewis catalyst complexes.

Although Applicant contemplates that the catalysts of the instant invention will have broad utility in the production of many types of asymmetric products, their utility is demonstrated, for example, by way of the following four types of reactions:

1) Addition of nucleophiles to meso epoxides proceeds in up to 85% enantiomeric excess:

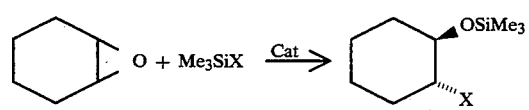

Typical reaction conditions in the above reaction scheme are provided in Examples 2, 14, 15, and 16 below. Suitable nucleophiles include but are not limited to trialkylsilyl azides, trialkylsilyl cyanides, and thiols.

2) Kinetic resolution of racemic epoxides is also based on nucleophilic addition, for example:

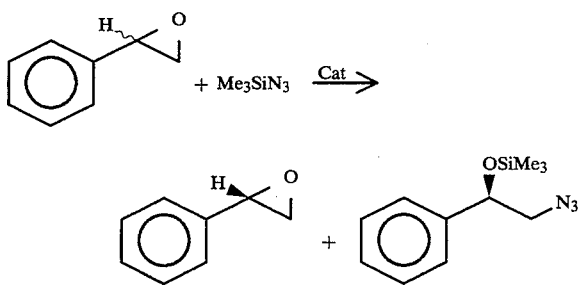

Typical conditions of this reaction are given in Example 4 below.

3) The addition of trimethylsilyl cyanide to aryl aldehydes to give protected cyanohydrins:

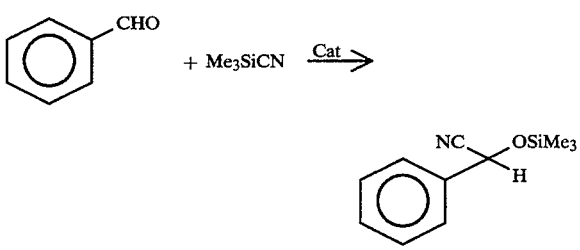

Typical reaction conditions are given in Examples 6 and 10 below. The products of this reaction scheme are known to be useful as intermediates in the manufacture of insecticides.

(4) The addition of organometalic reagents to aliphatic or aromatic aldehydes to give optically active alcohols or their derivatives:

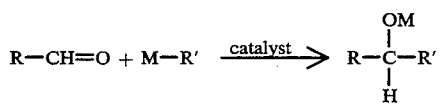

Typical reaction conditions are given in Examples 17 and 20 below.

Applicant contemplates that many other possible applications exist for these catalysts, including asymmetric Diels-Alder additions, asymmetric aldol condensations, 2+2 cycloadditions, ene reactions, catalytic hydride reduction of carbonyl groups, 1,2-addition of alkyl and aryl groups to carbonyl groups, and catalytic Michael additions to $\alpha,\beta$-unsaturated systems.

By the term "chiral", Applicant means "existing as a pair of enantiomers". These stereoisomers, designated the R and S isomers, are mirror images of one another. A chiral material may either contain an equal amount of the R and S isomers in which case it is called "racemic" or it may contain inequivalent amounts of R and S isomer in which case it is called "optically active".

By the term "optically active", Applicant means a compound which contains inequivalent amounts of the R and S enantiomers. The extent of this inequivalence is measured as the "enantiomeric excess".

By the term "enantiomeric excess", Applicant means the difference between the percent of R enantiomer and the percent of S enantiomer of an optically active compound. For example, a compound which contains 75% S isomer and 25% R isomer will have an enantiomeric excess of 50%. To provide highly selective reactions, the Lewis acid catalysts of the present invention should have an enantiomeric excess of at least about 90%.

By the term "enantioselective" Applicant means the ability to produce a product in an optically active form.

By the term "Lewis acid catalyst", Applicant means a catalyst which is able to accept an electron pair and in so doing enhances the electron deficiency of a reactant. The Lewis acid catalyst does not change its formal oxidation state during the course of the catalytic cycle.

In the following Examples, the term "trialkanolamine (2)" refers to a trialkanolamine of the formula

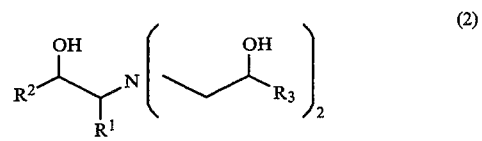

wherein $R^1$ is H or $CH_3$; and $R^2$ and $R^3$ are each independently $C_1$ to $C_{20}$ hydrocarbyl and may additionally have halogen, ether or ester groups. The term "dialkanolamine (3)" refers to a dialkanolamine of the formula

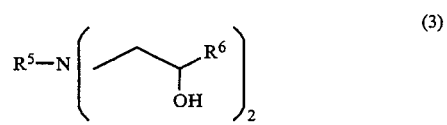

wherein $R^5$ may be H, or $C_1$ to $C_{20}$ hydrocarbyl additionally having halogen, ether or ester functional groups; and $R^6$ may be $C_1$ to $C_{20}$ hydrocarbyl additionally having halogen, ether or ester functional groups.

EXAMPLE 1

Preparation of Hydrolyzed Zirconium Catalyst

A solution containing trialkanolamine (2) ($R^1$=H; $R^2$ and $R^3$=$CH_3$) was prepared by treating S-1-amino-2-propanol (0.75 g, 10 mmol) with (S)-propylene oxide (1.28 g, 20 mmol) in toluene (3.0 mL) and allowing the mixture to stand for 6 days. This solution was added to a solution of zirconium (IV) tert-butoxide (3.84 g, 10 mmol) in dry tetrahydrofuran, rinsing with additional THF (5.0 mL). The mixture was stirred 1 h and the solvent was removed at reduced pressure. Hexane (10 mL) was added and evaporated at reduced pressure to promote removal of by-product alcohols. The resultant off-white solid was dissolved in tetrahydrofuran (25 mL). Water (180 $\mu$L, 10 mmol) was added to the stirred solution over the course of 1 min. The mixture was stirred 1 h and the solvent was removed at reduced pressure. Hexane (5 mL) was added and then removed at reduced pressure. The residue was taken up in hexane (25 mL), was filtered, and then the solvent was removed at reduced pressure to give the off-white solid catalyst (3.10 g). Anal.: C, 39.11; H, 6.58; N, 4.21.

EXAMPLE 2

Catalysis of Azide Addition to Cyclohexene Oxide

A sample of the catalyst (0.03 g) of Example 1 was placed in a vial to which was added a solution of azidodimethylisopropylsilane (0.18 g, 1.26 mmol) and cyclohexene oxide (0.12 g, 1.22 mmol) in 1,2-dichlorobutane (3.0 mL). The mixture was placed in a refrigerator at 4° C. for 4 days. Gas chromatographic analysis on a Cyclodex B chiral capillary column (J &

W Scientific, Folsom, Calif.) indicated the formation of (1S, 2S) -1-azido-2-(isopropyldimethylsiloxy)cyclohexane (91% yield, 85% enantiomeric excess).

EXAMPLE 3

Preparation of "Non-Hydrolyzed" Zirconium Catalyst

The trialkanolamine (2) ($R^1$=methyl; $R^2$ and $R^3$=phenyl) was prepared by heating a mixture of (R)-(+)-styrene oxide (2.40 g, 20 mmol) and (1R,2S)-(−)-norephedrine (1.51 g, 10 mmol) in benzene (5.0 mL) at 60° C. for 5 days followed by flash chromatography on 230–400 mesh silica with 45:5:50 ethyl acetate/triethylamine/toluene. A portion of the trialkanolamine (1.51 g, 3.86 mmol) was added to a solution of zirconium n-propoxide (1.80 g of 70% solution in n-propanol, 3.85 mmol) in toluene (25 mL) and the mixture was stirred 1 h. The solvent was removed at reduced pressure whereupon hexane (10 mL) was added and removed at reduced pressure to give the catalyst (1.86 g) as an off-white solid. Anal. C, 60.62; H, 6.87; N, 2.26.

EXAMPLE 4

Kinetic Resolution of Styrene Oxide

To a vial containing zirconium catalyst (0.05 g) prepared as in Example 3 was added a solution of azidotrimethylsilane (0.15 g, 90% pure, 1.17 mmol) and racemic styrene oxide (0.24 g, 2.0 mmol) in 1,2-dichloroethane (5.0 mL). After 5 days, gas chromatographic analysis on a Cyclodex B capillary column indicated that the styrene oxide remaining in the solution was enriched in the (R)-(+)-isomer and that the enantiomeric excess was 54.6%.

EXAMPLE 5

Preparation of Chiral Hafnium Catalyst

A solution of trialkanolamine (2) ($R^1$=H; $R^2$ and $R^3$=$CH_3$) (10 mmol) in toluene (3 mL) prepared as in Example 1 was added to a stirred solution of hafnium (IV) isopropoxide (4.15 g, 10 mmol) in tetrahydrofuran (20 mL), rinsing with additional THF (5 mL). After 1 h, the solvent was distilled away whereupon hexane (10 mL) was added and subsequently also removed at reduced pressure. The residue was redissolved in tetrahydrofuran (25 mL) and water (175 µL) was added over the course of 1 minute. After 1 h, the solvent was distilled away under reduced pressure whereupon hexane (5 mL) was added and subsequently also removed at reduced pressure. The crude residue was taken up in hexane (25 mL) and insoluble material (2.05 g) was separated by filtration. Distillation of the solvent from the soluble portion afforded the catalyst (1.23 g). Anal. C, 36.37; H, 5.92; N, 4.00.

EXAMPLE 6

Asymmetric Catalysis of Cyanohydrin Formation

A sample of the catalyst (0.05 g) of Example 5 was placed in a vial to which was added a solution of trimethylsilyl cyanide (0.20 g, 2.0 mmol) and m-phenoxybenzaldehyde (0.40 g, 2.0 mmol) in toluene (5.0 mL). After 2 days the solvent was removed at reduced pressure. Flash chromatography on 230–400 mesh silica gel with 90:10 hexane/ethyl acetate afforded a colorless oil which was shown to be m-phenoxybenzaldehyde cyanohydrin trimethylsilyl ether by NMR comparison with an authentic sample. The optical rotation of a heart cut from fractions 10–12 (c=10 in chloroform at 20° C.) was $[\alpha]_D$= +3.3° indicating that the enantiomeric excess was 19%.

EXAMPLE 7

Preparation of Titanium Catalyst

A solution of trialkanolamine (2) ($R^1$=H; $R^2$ and $R^3$=methyl) (10 mmol) in toluene (3 mL) prepared as in Example 1 was added to a solution of titanium (IV) isopropoxide (2.84 g, 10 mmol) in toluene (10 mL). After 10 min the solvent was distilled off at reduced pressure to afford a white crystalline solid identified as L-Ti-O$^i$Pr. Anal. Calc'd for $C_{12}H_{25}NO_4Ti$: C, 48.82; H, 8.54; N, 4.74. Found: C, 48.39, 48.41; H, 8.20, 8.13; N, 4,75. $^1$H NMR ($C_6D_6$): 1.10 (d, J=7, 9H), 1.35 (d, J=7, 6H), 2.85–2.95 (m, 6H), 4.62 (septet, J=7, 1H), 4.91 (m, 3H).

EXAMPLE 8

Preparation of Vanadium Catalyst

In a flask was placed trialkanolamine (2) ($R^1$=H; $R^2$ and $R^3$=cyclohexyl) (0.39 g, 1.0 mmol), tri-n-propyl vanadate (0.24 g, 1.0 mmol), and tetrahydrofuran (10 mL). After 1 h a white solid had precipitated which was collected by filtration and dried in vacuo and shown to have the composition L-V=O. Anal. Calc'd for $C_{24}H_{42}NO_4V$: C, 62.73; H, 9.21; N, 3.05.Found: C, 62.59; H, 8.92; N, 3.04. $^{13}$C NMR ($CDCl_3$): δ25.96, 26.10, 26.43, 28.83, 29.03, 43.51, 57.77, 89.00.

EXAMPLE 9

Preparation of Zr Catalyst from Cyclohexyl Ligand

To a flask containing trialkanolamine ligand (2) ($R^1$=methyl; $R^2$ and $R^3$=cyclohexyl) (1.26 g, 3.08 mmol) was added a solution of commercial zirconium n-propoxide (1.44 g of 70% pure material, 3.08 g) in tetrahydrofuran (15 mL). After standing overnight the solvent was distilled off at reduced pressure. Hexane (10 mL) was added and distilled away to aid in removal of remaining n-propanol. The residue was a white solid with a complex $^{13}$C NMR spectrum whose composition corresponded approximately to that of L-Zr-O$^n$Pr. Anal. Calc'd for $C_{28}H_{51}NO_4Zr$: C, 60.38; H, 9.23; N, 2.51.Found: C, 59.47; H, 9.27; N, 2.78.

EXAMPLE 10

Low Temperature Cyanohydrin Synthesis

A round-bottomed flask equipped with a septum-covered side arm was charged with a solution of trimethylsilyl cyanide (0.20 g, 2.02 mmol) and m-phenoxybenzaldehyde (0.40 g, 2.02 mmol) in toluene (4.0 mL). The flask was cooled to −78° C. under an atmosphere of dry nitrogen and a hypodermic syringe was used to inject a solution of catalyst (0.05 g) prepared according to Example 9 in toluene (1.0 mL). The mixture was maintained at −78° C. for 8 h and was then allowed to warm to room temperature overnight. The solvent was removed at reduced pressure and the product was isolated by flash chromatography in 90:10 hexane/ethyl acetate and was shown to be m-phenoxybenzaldehyde cyanohydrin trimethylsilyl ether by NMR comparison with an authentic sample. The optical rotation of this material (c=8 in chloroform at 20° C.) was $[\alpha]_D$= −10.4°. A sample of the product was derivatized with camphanic chloride and analyzed by HPLC on a Bakerbond Chiralcel OB column (J. T. Baker Inc., Phillipsburg, N.J.) at 60° C. with 83:17 hexane/isopropanol as eluting solvent and UV detection at 254 nm. The enantiomeric excess was 59%.

EXAMPLE 11

Zirconium Catalyst where Trialkanolamine Ligand Contains Ether Functionality

The trialkanolamine (2) ($R^1$=H; $R^2$ and $R^3$=benzyloxymethyl) was prepared by treating a solution of (S)-(+)-2-(benzyloxymethyl)oxirane (2.0 g, 12.2 mmol) in methanol (3.0 mL) with a 2N solution of ammonia in methanol (2.0 mL, 4.0 mL) for 7 days at 50° C. follow by distillation of the solvent. The resultant trialkanolamine (2.16 g material containing some residual solvent, 3.9 mmol) was treated with a solution of commercial zirconium n-propoxide (1.81 g of 70% pure material, 3.9 mmol). in toluene (10 mL). After 1 h the solvent was distilled off at reduced pressure; hexane (15 mL) was added and distilled off to aid in the removal of residual n-propanol. The product was a semi-solid. Using this catalyst, kinetic resolution of styrene under the conditions of Example 4 produced (S)-(−)-styrene oxide in 23% enantiomeric excess.

EXAMPLE 12

Preparation of Hydrolyzed Niobium Catalyst

A solution of trialkanolamine (2) ($R^1$=H; $R^2$ and $R^3$=methyl) (10 mmol) in toluene (3.0 mL) prepared as in Example 1 was added to a solution of niobium ethoxide (3.18 g, 10 mmol) in tetrahydrofuran (25 mL). After 1 h the solvent was distilled off at reduced pressure; hexane (10 mL) was added and distilled away to aid in the removal of by-product ethanol. The residue was redissolved in tetrahydrofuran (25 mL) and water (180 µL, 10 mmol) was added. After 1 h the solvent was removed in the same manner as before to afford a white solid identified as L-Nb(O)2Nb-L by its NMR spectrum and analysis. $^1$H NMR (CDCl$_3$): δ 1.04 (d, J=7 Hz, 6H), 1.15 (d, J=7 Hz, 6H), 1.47 (d, J=7 Hz, 6H), 2.45–2.60 (m, 4H), 2.80–2.95 (m, 4H), 3.2–3.4 (m, 4H), 4.95 (m, 2H), 4.70 (m, 2H), 5.62 (m, 2H). Anal. Calc'd for C$_9$H$_{18}$NO$_4$Nb: C, 36.38; H, 6.11; N, 4.71. Found: C, 34.44; H, 5.65; N, 4.19.

EXAMPLE 13

Preparation of Hydrolyzed Tantalum Catalyst

A solution of R,R,R-triisopropanolamine (0.57 g, 3.0 mmol) in tetrahydrofuran (10 mL) was added all at once to a solution of tantalum ethoxide (1.22 g, 3.0 mmol) in tetrahydrofuran (10 mL). After 1 h the solvent was distilled off at reduced pressure. A small sample of the residue was removed and was shown to be L-Ta(OEt)$_2$, $^1$H NMR (C$_6$D$_6$): δ 1.13 (d, J=7 Hz, 9H), 1.28 (t, J=7 Hz, 6H), 2.33 (d, J=8 Hz, 6H), 4.56 (q, J=7 Hz, 4H), 4.55–4.68 (m, 3H). The remainder was treated with water (50 µL, 2.8 mmol) in tetrahydrofuran (10 mL). After 1 h the solvent was distilled off at reduced pressure; hexane (10 mL) was added and distilled away to aid in the removal of side-product ethanol. The residue was a white solid which was identified as L-Ta(O)2Ta-L by its analysis and NMR spectrum. Anal. Calc'd for C$_9$H$_{18}$NO$_4$Ta: C, 28.06; H, 4.71; N, 3.64. Found: C, 27.43; H, 4.18; N, 3.89. $^1$H NMR (CDCl$_3$): δ 1.02 (d, J=7 Hz, 6H), 1.15 (d, J=7 Hz, 6H), 1.44 (d, J=7 Hz, 6H), 2.45–2.65 (m, 4H), 2.8–2.9 (m, 4H), 3.23–3.34 (m, 4H), 4.48 (m, 2H), 4.79 (m, 2H), 5.49 (m, 2H).

EXAMPLE 14

Addition to Acyclic Meso Epoxide

To a vial containing niobium catalyst (0.05 g) prepared as in Example 12 was added a solution of azidotrimethylsilane (0.28 g, of material of nominal 90% purity, 2.2 mmol) and cis-2,3-epoxybutane (0.14 g, 1.9 mmol) in 1,2-dichloroethane (3.0 mL). The mixture was allowed to stand 5 days at room temperature. Gas chromatographic analysis on a Cyclodex B capillary column indicated the formation of (2R,3R)-2-azido-3-(trimethylsilyloxy)butane in 15% enantiomeric excess.

EXAMPLE 15

Asymmetric Addition of Trimethylsilyl Cyanide

To a vial containing hydrolyzed zirconium catalyst (0.03 g) prepared as in Example 1 was added a solution of cyclohexene oxide (0.12 g, 1.2 mmol) and trimethylsilyl cyanide (0.15 g, 1.5 mmol) in 1,2-dichlorobutane (3.0 mL). The mixture was allowed to stand overnight at room temperature. Gas chromatographic analysis on a Cyclodex B capillary column indicated the formation of (1S,2S)-1-cyano-2-(trimethylsilyloxy)cyclohexane in 33% enantiomeric excess.

EXAMPLE 16

Asymmetric Addition of Thiocresol

To a vial containing hydrolyzed zirconium catalyst (0.03 g) prepared as in Example 1 was added a solution of cyclohexene oxide (0.12 g, 1.2 mmol) and p-thiocresol (0.15 g, 1.2 mmol) in 1,2-dichloropropane (3.0 mL). The mixture stood for 3 days at room temperature whereupon the solvent was removed at reduced pressure and the residue was subjected to flash chromatography in 80:20 hexane/ethyl acetate. Fractions 13–16 were found to contain (1R,2R)-2-(p-tolylthio)cyclohexanol (0.16 g, 60%). The optical rotation of the material from cuts 13–14 (c=5 in dichloromethane at 23° C.) was $[\alpha]_D$=−11.6° indicating an enantiomeric excess of 18%.

EXAMPLE 17

Asymmetric Addition of Diethylzinc to Benzaldehyde

A stock solution was prepared containing benzaldehyde (1.06 g, 10 mmol), diethylzinc (10.0 mL of 1N hexane solution, 10 mmol), and t-butylbenzene as internal standard (1.00 g), in toluene (20 mL). In a vial was placed niobium catalyst (0.01 g) prepared as in Example 12 and to this was added a portion of the stock solution (1.00 mL). After 24 h at room temperature the mixture was acetylated by addition of acetic anhydride (100 µL) and analyzed by gas chromatography on a Cyclodex B capillary column. Analysis indicated that 1-phenylpropyl acetate had formed in 97% yield and 51% enantiomeric excess.

EXAMPLE 18

Preparation of Hydrolyzed Titanium Complex with Dialkanolamine Ligand

Dialkanolamine (3) ($R^5$=4-methylbenzyl; $R^6$=methyl) was prepared by reaction of 4-methyl-benzylamine with (S)-propylene oxide in benzene followed by flash chromatography in 45:5:50 ethyl acetate/triethylamine/toluene. To a solution of titanium (IV) isopropoxide (0.91 g, 3.67 mmol) in tetrahydrofuran (10 mL) was added a solution of the dialkanolamine (0.87 g, 3.67 mmol) in tetrahydrofuran (10 mL). After 1 h the solvent was removed at reduced pressure; hexane (10 mL) was added and distilled away to facilitate removal of the last traces of isopropanol. The residue was redissolved in tetrahydrofuran (15 mL) and water (66 μL, 3.67 mmol) was added. Distillation of the solvent and hexane treatment as above gave a fine white powder. The product was identified as the complex L-Ti(O)Ti-L by its NMR spectrum and elemental analysis. Anal. Calc'd. for $C_{28}H_{42}N_2O_6Ti_2$: C, 56.20; H, 7.07; N, 4.68. Found: C, 58.85; H, 7.06; N, 4.36.

EXAMPLE 19

Preparation of Hydrolyzed Zirconium Catalyst with Dialkanolamine Ligand

A solution of dialkanolamine (3) ($R^5$=4-methylbenzyl; $R^6$=methyl) (1.05 g, 4.5 mmol) in tetrahydrofuran (10 mL) was added to a solution of zirconium (IV) t-butoxide (1.70 g, 4.4 mmol). After 1 h the solvent was removed at reduced pressure; hexane (10 mL) was added and distilled away to facilitate removal of the last traces of t-butyl alcohol. The gummy residue was redissolved in tetrahydrofuran (15 mL) and water (80 μL, 5.3 mmol) was added. After 0.5 h, distillation of the solvent and hexane treatment as above gave a white solid. Anal. Calc'd.: C, 50.69; H, 7.11; N, 3.18.

EXAMPLE 20

Asymmetric Addition of Diethylzinc Using Catalyst Containing Dialkanolamine Ligand A stock solution was prepared containing benzaldehyde (1.06 g, 10 mmol), diethylzinc (10.0 mL of 1N hexane solution, 10 mmol), and t-butylbenzene (1.00 g) as internal standard in toluene (20 mL). To a vial containing hydrolyzed titanium catalyst (0.01 g) prepared as in Example 18 was added a portion of the stock solution (1.0 mL). After 24 h at room temperature the mixture was acetylated by addition of acetic anhydride (100 μL) and analyzed by gas chromatography on a Cyclodex B capillary column. Analysis indicated that 1-phenylpropyl acetate was formed in 97% yield and 90.6% enantiomeric excess.

What is claimed is:

1. An optically active trialkanolamine comprising formula (2)

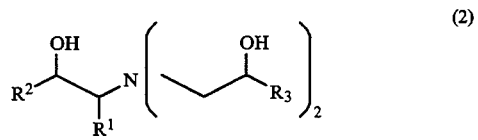

wherein:
$R^1$ is H or $CH_3$;
$R^2$ and $R^3$ are each independently $C_1$ to $C_{20}$ hydrocarbyl and may additionally have halogen, ether, or ester groups;
provided that $R^1$ is $CH_3$ when $R^2$ and $R^3$ are each $CH_3$.

2. An optically active trialkanolamine of claim 1, wherein:
$R^1$ is methyl; and
$R^2$ and $R^3$ are each phenyl.

3. An optically active trialkanolamine of claim 1, wherein:
$R^1$ is H; and
$R^2$ and $R^3$ are each cyclohexyl.

4. An optically active trialkanolamine of claim 1, wherein:
$R^1$ is H; and
$R^2$ and $R^3$ are each benzyloxymethyl.

* * * * *